US012165052B2

(12) United States Patent
Khullar et al.

(10) Patent No.: US 12,165,052 B2
(45) Date of Patent: Dec. 10, 2024

(54) INTERPRETABLE NEURAL NETWORKS FOR CUFFLESS BLOOD PRESSURE ESTIMATION

(71) Applicant: Apple Inc., Cupertino, CA (US)

(72) Inventors: Siddharth Khullar, San Jose, CA (US); Nicholas E. Apostoloff, San Jose, CA (US); Amruta Pai, Houston, TX (US)

(73) Assignee: Apple Inc., Cupertino, CA (US)

( * ) Notice: Subject to any disclaimer, the term of this patent is extended or adjusted under 35 U.S.C. 154(b) by 659 days.

(21) Appl. No.: 16/945,695

(22) Filed: Jul. 31, 2020

(65) Prior Publication Data

US 2021/0117782 A1    Apr. 22, 2021

Related U.S. Application Data

(60) Provisional application No. 62/923,393, filed on Oct. 18, 2019.

(51) Int. Cl.
*G06N 3/08* (2023.01)
*G06N 3/045* (2023.01)
*G16H 40/60* (2018.01)

(52) U.S. Cl.
CPC .............. *G06N 3/08* (2013.01); *G06N 3/045* (2023.01); *G16H 40/60* (2018.01)

(58) Field of Classification Search
CPC ........ G06N 3/0454; G06N 3/08; G06N 3/082; G16H 40/60; G16H 50/70; G16H 50/30
See application file for complete search history.

(56) References Cited

U.S. PATENT DOCUMENTS

| | | |
|---|---|---|
| 6,918,879 B2 | 7/2005 | Ting et al. |
| 9,603,524 B2 | 3/2017 | Park et al. |
| 9,943,263 B2 | 4/2018 | Lee |
| 10,517,489 B2 | 12/2019 | Narasimhan et al. |
| 10,559,220 B2 | 2/2020 | Wisbey |
| 2013/0267796 A1 | 10/2013 | Enric Monte Moreno |
| 2015/0038856 A1* | 2/2015 | Houlton ............. A61B 5/02028 600/484 |

(Continued)

FOREIGN PATENT DOCUMENTS

CN    102397064 B    2/2014

OTHER PUBLICATIONS

Liu, K et al., "Understanding Individual Neuron Importance Using Information Theory" (Year: 2018).*

(Continued)

*Primary Examiner* — Alexey Shmatov
*Assistant Examiner* — Devika S Maharaj
(74) *Attorney, Agent, or Firm* — Kubota & Basol LLP

(57) ABSTRACT

In some examples, an individually-pruned neural network can estimate blood pressure from a seismocardiogram (SCG). In some examples, a baseline model can be constructed by training the model with SCG data and blood pressure measurement from a plurality of subjects. One or more filters (e.g., the filters in the top layer of the network) can be ranked by separability, which can be used to prune the model for each unseen user that uses the model thereafter, for example. In some examples, individuals can use individually-pruned models to calculate blood pressure using SCG data without corresponding blood pressure measurements.

18 Claims, 7 Drawing Sheets

(56) References Cited

U.S. PATENT DOCUMENTS

| | | | |
|---|---|---|---|
| 2017/0181649 A1 | 6/2017 | Carter et al. | |
| 2017/0238818 A1* | 8/2017 | Gaurav | A61B 5/7264 |
| 2018/0116600 A1 | 5/2018 | Basu et al. | |
| 2018/0300631 A1* | 10/2018 | Roy | G06N 3/088 |
| 2019/0104951 A1 | 4/2019 | Valys et al. | |
| 2019/0209022 A1* | 7/2019 | Sobol | A61B 5/0022 |
| 2020/0054290 A1* | 2/2020 | Jang | A61B 5/1102 |
| 2020/0330050 A1* | 10/2020 | Peters | G16H 40/40 |
| 2021/0056413 A1* | 2/2021 | Cheung | G06N 3/0454 |
| 2021/0375473 A1 | 12/2021 | Gatys et al. | |

OTHER PUBLICATIONS

Northcutt, C. et al., "Learning with Confident Examples: Rank Pruning for Robust Classification with Noisy Labels" (Year: 2017).*

Das, S. et al., "Hypertension Diagnosis: A Comparative Study using Fuzzy Expert System and Neuro Fuzzy System" (Year: 2013).*

Zeng, X. et al., "Hidden neuron pruning of multilayer perceptrons using a quantified sensitivity measure" (Year: 2005).*

International Search Report received for PCT Patent Application No. PCT/US2021/035304, mailed on Sep. 16, 2021, 6 pages.

Ding et al., "Continuous Blood Pressure Measurement from Invasive to Unobtrusive: Celebration of 200th Birth Anniversary of Carl Ludwig", Available online at: <https://spiral.imperial.ac.uk/bitstream/10044/1/43660/2/Continuous%20Blood%20Pressure%20Measurement%20from%20Invasive%20to%20Unobtrusive%20Celebration%20of%20200th%20Birth%20Anniversary%20of%20Carl%20Ludwig%20-%20rev.pdf>, Oct. 25, 2016, 13 pages.

Taebi et al., "Recent Advances in Seismocardiography", Vibration, Available online at: <https://webcache.googleusercontent.com/search?q=cache:hw6Z7jSDQEgJ:https://www.mdpi.com/2571-631X/2/1/5/pdf+&cd=1&hl=en&ct=clnk&gl=us&client=firefox-b-1-d>, Jan. 14, 2019, 23 pages.

Non-Final Office Action received for U.S. Appl. No. 17/336,188, mailed on Mar. 7, 2023, 16 pages.

Final Office Action received for U.S. Appl. No. 17/336,188, mailed on Sep. 20, 2023, 18 pages.

* cited by examiner

INTERPRETABLE NEURAL NETWORKS FOR CUFFLESS BLOOD PRESSURE ESTIMATION

CROSS-REFERENCE TO RELATED APPLICATIONS

This application claims the benefit of U.S. Provisional Application No. 62/923,393, filed Oct. 18, 2019, the contents of which is hereby incorporated by reference in its entirety for all purposes.

FIELD OF THE DISCLOSURE

This relates to neural networks and more particularly to estimating blood pressure using an individually-pruned neural network that accepts a seismocardiogram (SCG) as input.

BACKGROUND OF THE DISCLOSURE

Heart disease and stroke may account for 1 in 3 deaths in the United States. Blood pressure can be measured and monitored using a blood pressure cuff, or one of a plurality of other methods and instruments available to patients.

Neural networks can be used to process data across a plurality of applications, such as image processing, speech recognition, and health. A neural network can consist of a plurality of layers (or levels), each including a plurality of filters (or neurons). Neural networks can be trained by being provided with training data that includes input data and the desired output. Once a neural network has been trained, further input data can be provided to the network, which can produce an output according to the learning achieved by the model during training.

SUMMARY

This relates to neural networks and more particularly to estimating blood pressure using an individually-pruned neural network that accepts a seismocardiogram (SCG) as input. In some examples, a baseline model can be constructed by training the model with SCG data and blood pressure measurement from a plurality of subjects. One or more filters (e.g., the filters in the top layer of the network) can be ranked by separability, which can be used to prune the model for each unseen user that uses the model thereafter, for example. In some examples, the unseen user can provide the baseline model with a set of SCG data and blood pressure measurements and the mean absolute error of the predicted blood pressure can be evaluated for a plurality of runs using the model with an increasing number of filters ranked by separability. In some examples, including low-separability filters in the model can decrease the accuracy of the model. Therefore, the model can be pruned to include the optimal number of filters ranked by separability for each individual, for example. In some examples, the individual can use the pruned model to calculate blood pressure using SCG data without corresponding blood pressure measurements.

DETAILED DESCRIPTION

In the following description of examples, reference is made to the accompanying drawings which form a part hereof, and in which it is shown by way of illustration specific examples that can be practiced. It is to be understood that other examples can be used and structural changes can be made without departing from the scope of the disclosed examples.

Figure 1:
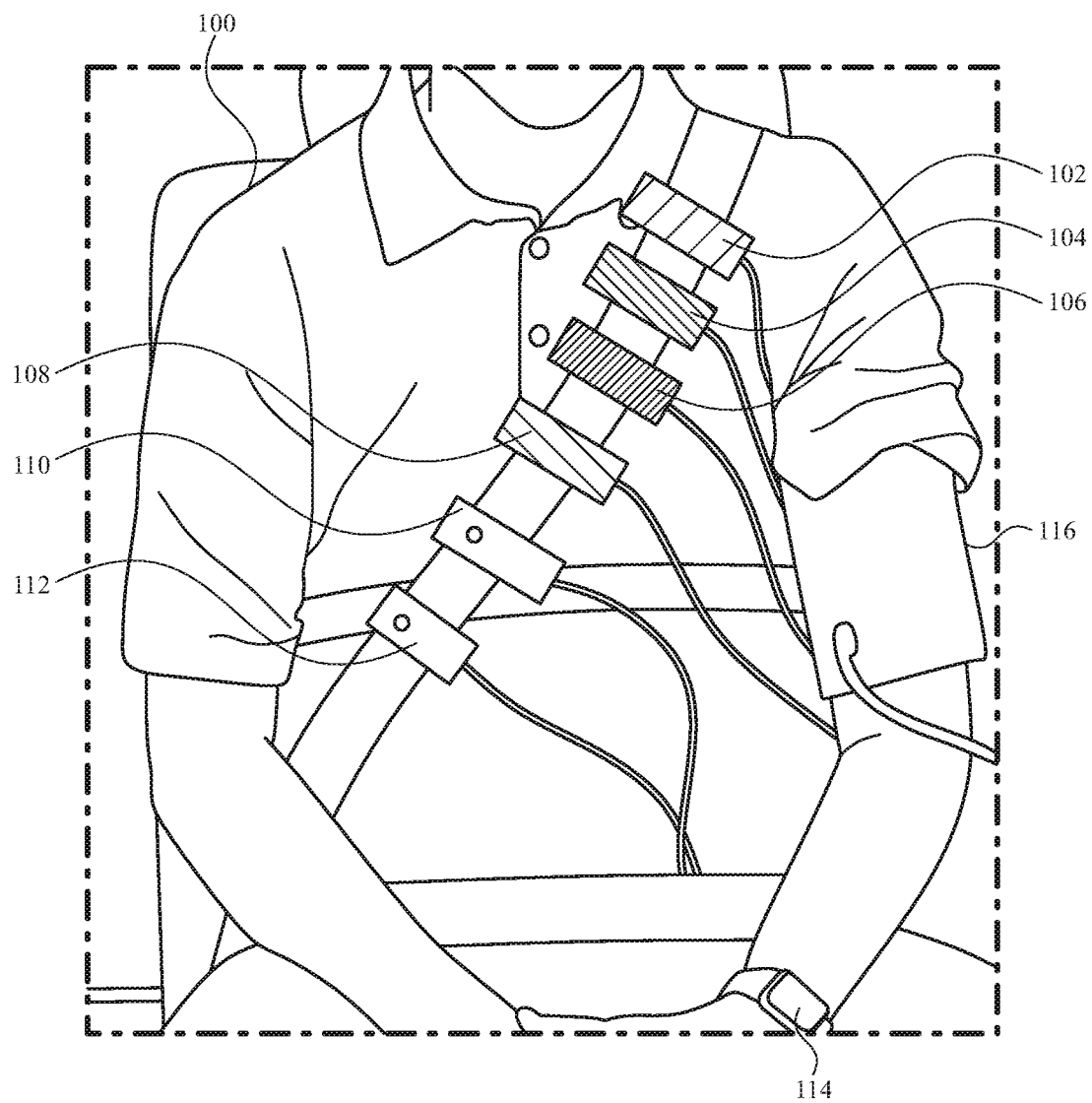
FIG. 1 illustrates exemplary instrumentation for measuring blood pressure according to some examples of the disclosure.

FIG. 1 illustrates exemplary instrumentation for measuring blood pressure according to some examples of the disclosure. As shown in FIG. 1, a subject 100 can be outfitted with a plurality of inertial measurement units (IMUs) 102-112, a wearable electronic device 114, and a blood pressure cuff 116. The IMUs 102-112 can be positioned across the subject's 100 chest and the wearable device 114 can be worn on the subject's 100 wrist. In some examples, other sensor locations and/or configurations are possible.

The IMUs 102-112 can measure inertial motion (e.g., acceleration and rotational rate) of the subject 100 and can communicate the information to one or more processors. For example, the IMUs 102-112 can be 3-axis IMUs that can detect the z-axis direction movements, the y-axis direction movements, and the x-axis direction movements. In some examples, the IMUs 102-112 can each include one or more sensors (e.g., a 3-axis gyroscope) to detect rotational movement for a total of 6 axes. The IMUs 102-112 can determine the acceleration and rotational movement using only accelerometers and gyroscopes to determine the pitch, roll, and yaw of the subject 100. In some examples, the IMUs may or may not include magnetometers.

The blood pressure cuff 114 can be used to provide training data to an artificial neural network to train the artificial neural network to calculate the subject's blood pressure 100 based on accelerometer and/or gyroscope data provided by one or more IMUs 102-112 or a wearable device 114. For example, the blood pressure cuff 116 can collect blood pressure measurements while the one or more IMUs 102-112 and/or the wearable device 114 can collect accelerometer and/or gyroscope data. This data can be provided to the artificial neural network to train the artificial neural network to determine blood pressure based on accelerometer and/or gyroscope data.

In some examples, the motion data is collected by the one or more IMUs 102-112 positioned across the chest of the subject 100. In some examples, a wearable device, such as wearable device 114 can be used to measure motion data. For example, a wearable device 114 worn on the wrist can be used by instructing the subject 100 to position their wrist over their chest during data collection. Other wearable devices, such as devices worn on the torso or at a different position on the arm (such as the forearm location of cuff 116) that collect motion data are possible.

Figure 2:
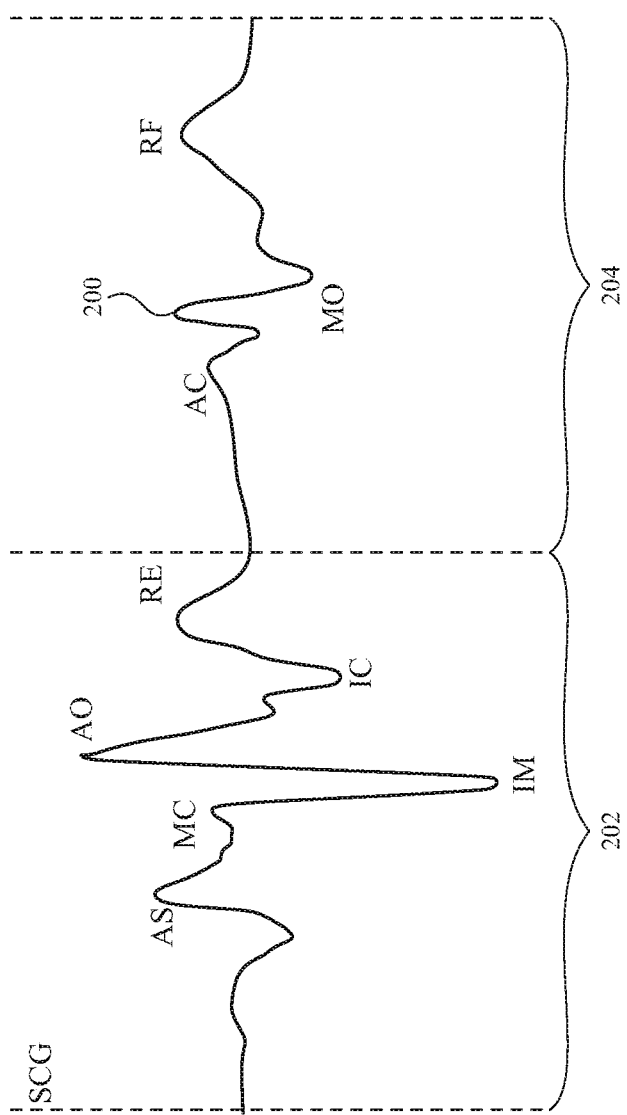
FIG. 2 illustrates an exemplary Seismocardiogram (SCG) that can be used to determine blood pressure according to some examples of the disclosure.

FIG. 2 illustrates an exemplary Seismocardiogram (SCG) 200 that can be used to determine blood pressure according to some examples of the disclosure. For example, SCG 200 can be accelerometer data captured during one heartbeat of the subject 100. In some examples, SCG 200 can be generated using one or more IMUs 102-114 or a wearable device 114. The SCG 200 can include a plurality of fiducial points indicated in FIG. 2. The artificial neural network can identify one or more fiducial points and use the timing between two or more points to estimate blood pressure. Moreover, the SCG 200 can be used to identify the systole phase 202 and diastole phase 204 of the heartbeat.

An example procedure for constructing, training, and evaluating the model will now be described. The exemplary dataset can contain 13 participants (e.g., Age: 38 7; Gender (M/F): 11/2). For measurement of SCG, 4 inertial measurement units, can be placed across the chest over the clothing. The participants can each perform 12 different sessions of sedentary activities, such as rest, reclined seating, talking on phone, watching videos, drinking water, chewing gum, and typing on laptop, all while staying seated. Each session can be 2 minutes in length with time-series sensors recording at a sampling frequency of 200 Hz, for example. For reference measurements, a Biopac MP150 system with two-lead ECG and an abdomen belt to capture respiration rate can be used. In some examples, an inflatable oscillometric blood pressure arm cuff (e.g., blood pressure cuff 166) can be used to obtain the reference BP readings before data capture, between each of the 12 sessions, and at the end of last session. Thus, 13 reference readings can be collected per participant over a total duration of 30 minutes. The blood pressure variability among the 13 subjects can be summarized as SBP: 118+/−12, Range: 82-165, DBP: 83+/−9, Range: 50-130 mmHg. For the four accelerometer sensors, slow-varying DC changes (e.g., due to respiration, sliding in seat etc.) can be removed using a filter, such as a 3rd order Butterworth bandpass filter with a passband of F$\omega$=0.75 30 Hz. In some examples, about 10% of the data can be rejected from training set in each fold due to large transient motions in the upper body (e.g. reaching for phone, stretching etc.).

The generalization capability of the neural network can be tested using leave-one-out cross validation, where all data from subject-n is held out for testing in fold-n (n=1, 2 . . . 13). From the 2 min sequences, 10 second input samples can be generated by stacking the 3 axial signals from the sensor. Each input sample, Xi can be of size 2000×3. For added robustness against variability due to sensor positioning, samples can be drawn from the set of four sensors.

In some examples, an artificial neural network can be constructed to determine systolic and diastolic blood pressure of the patient from an SCG. For example, an SCG similar to SCG 200 that includes multiple heartbeats can be used. Some examples are based on the intuition that a higher-order latent space carrying information about the pressure in the system can be derived from a mechanical representation (e.g., an SCG) of cardiovascular function. An exemplary proposed end-to-end network, summarized in Table 1 can operate on SCG data, and can include four 1D convolutional blocks (CONV), each with a batch-normalization step, two fully-connected layers (FC) and a penultimate layer with 2 outputs (SBP and DBP). In some examples, the hyper-parameters (stride and kernel size) for the CONV blocks are designed in relation to the known morphological features present in SCG signal. For example, a substantially large 1D kernel can be used in the first two layers (e.g., 51 samples ~250 ms), with different strides in the middle two layers, and dilated convolutions (dilation factor=2 in each layer) can be performed. This can assist with learning features at different scales, frequencies but can approximately cover the same temporal window. The number of filters for all CONV layers can be fixed to 32. In some examples, other network architectures can be used without departing from the scope of the disclosure.

TABLE 1

Network Architecture

| Layer Type Depth | Size, Filters | Stride | Output |
|---|---|---|---|
| conv1d 0 | 51, 32 | 1 | 2000 × 32 |
| conv1d 1 | 51, 32 | 2 | 1000 × 32 |
| conv1d 2 | 21, 32 | 2 | 500 × 32 |
| conv1d 3 | 11, 32 | 1 | 500 × 32 |
| flatten 4 | — | — | 16000 × 1 |
| fc 5 | 1800 | — | 1800 × 1 |
| fc 6 | 900 | — | 900 × 1 |
| output | 2 | — | 2 |

In some examples, the neural network can be trained using the collected data. The reference blood pressure measurements can be sparse (1 measurement every 2 mins) in some examples. For training, the blood pressure labels can be augmented with linear interpolation between measurements taken at the start and end of each session. This linear interpolation can be based on the assumption that the BP variations are slow in nature, especially under relatively sedentary conditions. After 10 repetitions of training, the hyperparameters can be set at batch-size: 400, epochs: 600. Mean-squared error (MSE) loss and an ADAM optimizer with learning rate: 10-4, E: 10-7, $\beta1$:0.9, $\beta2$:0.999, decay: 0 can be used. During training, data from training subjects can be split in to 80/20 ratio for training and validation. Each input batch (Xb: 400×2000×3, Yb: 400×2) can be formed by randomly sampling (without replacement) from the training data that contains 12 training subjects (X: 576×23000×3 and Y: 576×23000×2). The model can be implemented using Keras with Tensorflow backend or a suitable alternative. In some examples, other training procedures and data processing can be applied.

In some examples, the neural network can be validated using N-fold cross-validation over 13 folds. In some examples, the mean absolute error (MAE) for SBP and DBP values can be reported for each session in the data set. For example, the predicted SBP (e.g., calculated by the neural network) over a 30-second time-window can be calculated at the end of each session and compared with the BP reference reading (e.g., obtained from the blood pressure cuff 116) obtained at the end of each session.

In some examples where a small data set is used, the model may struggle to accurately predict low or high reference values. When there are fewer training examples for extreme BP reference readings, generalization can be challenging. Moreover, poor signal quality for one or more subjects can adversely affect the predictions. In some examples, the baseline model generated from the training data shows promise in its ability to encode information about blood pressure from raw SCG signals in an end-to-end manner. In some examples, to overcome some of the challenges with the baseline model, an interpretability-driven approach can be used to enable inter-subject adaptation and improved generalization of the baseline model.

Interpretability of machine learning models can be important for safety-critical and health applications (e.g., including blood pressure measurement). Interpretability can help users interpret model behavior using domain knowledge (commonly known as attribution), as well as discover which features may be important to the model (commonly called introspection). For example, each cardiac cycle contains two phases—systole and diastole that correspond to blood leaving and filling the ventricles, respectively. In some examples, the timing of these cycles can be derived from distinct fiducial points that manifest themselves in ECG and SCG (e.g., SCG 200 described above with reference to FIG. 2).

In some examples, it is possible to discover specific neurons in a neural network that respond to specific objects in an image. For example, this is similar to identifying neurons that behave like semantic concept detectors (e.g. trees, faces, etc.). In addition, in some examples, neural networks can provide insights on the decision reasoning and prediction failures. In some examples, it is possible to identify neurons that respond to the systole and diastole segments of a heartbeat. For example, systole and diastole masks can be generated for each input sample. Each mask can be a square wave that passes the portion of the SCG corresponding to the respective phase of the heartbeat. In some examples, the R-R interval (reference measurement) can be used to estimate the median length of the cardiac cycle, which can then be divided in to systole and diastole segments using a 40/60 ratio split. These segments can be assembled as binary masks M $(t)_c^i$, where concept $c \in \{systole, diastole\}$. For example, returning to FIG. 2, a mask for examining the systole phase 202 of the signal would have a value of 1 during the systole phase 202 and a 0 during the diastole phase 204. A mask for the diastole phase can have the opposite values.

Each input sample, $X(t)^i$ can be input to the network to yield embedding $A(t)_L^{i,j}$ for neuron j in layer L. Using these embedding and concept masks, two scalar metrics can be estimated, namely Relevance, Rj, and Separability, Sj. As shown in Eqn. 1, relevance can be estimated for each concept c and interpreted as the energy in systole or diastole phase of the signal with respect to total energy in the signal.

$$R_c^{i,j} = \frac{\frac{\sum_t A(t)^{i,j} M(t)_c^i}{\sum_t M(t)_c^i}}{\sum_{k=sys,dia} \frac{\sum_t A(t)^{i,j} M(t)_z^i}{\sum_t M(t)_z^i}}. \quad (1)$$

Figure 3A:
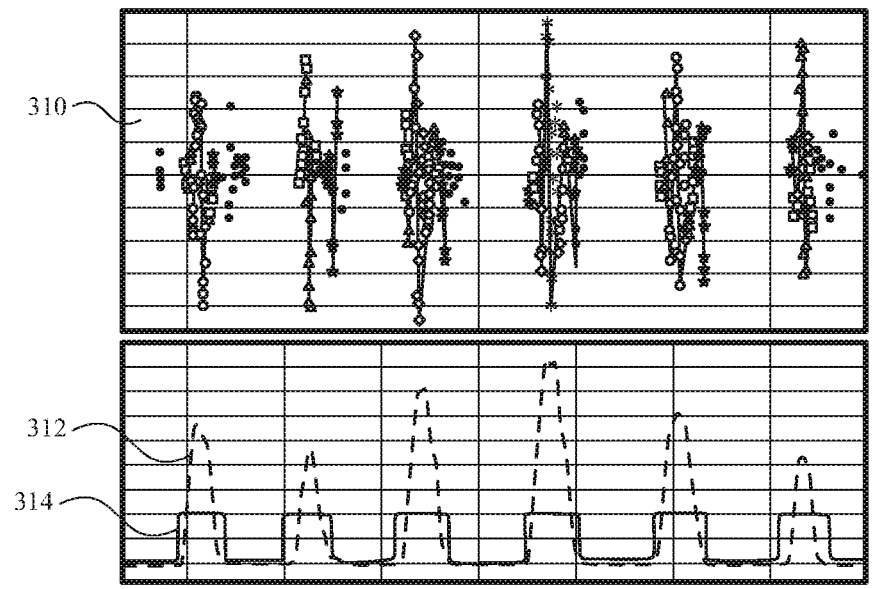
FIG. 3A illustrates the separability of neurons in an exemplary artificial neural network according to some examples of the disclosure.
Figure 3B:
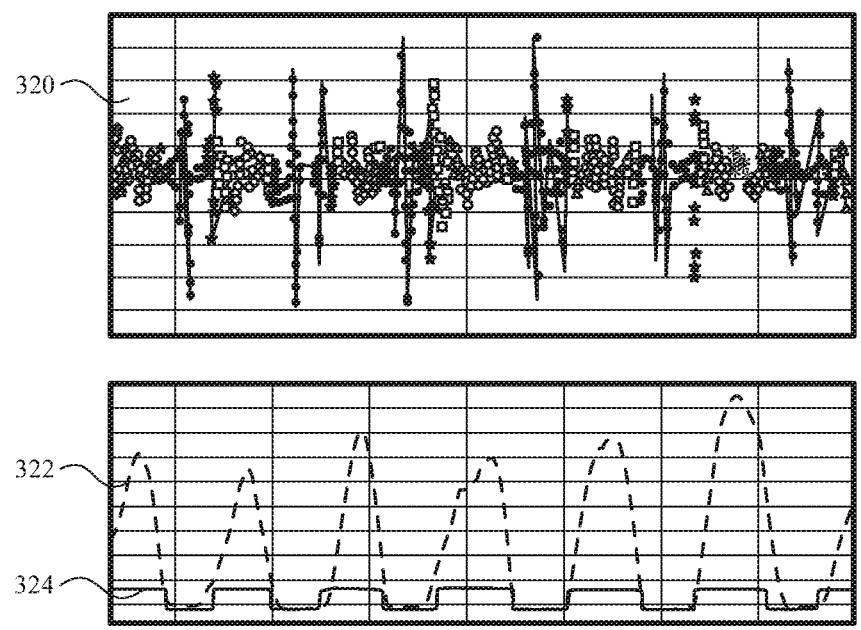
FIGS. 3B-3C illustrate exemplary filter activations as a heatmap of all filters and as a graph illustrating the raw activation of an exemplary highly relevant filters according to some examples of the disclosure.

FIGS. 3A-3B illustrate exemplary filter activations as a heatmap of all filters and as a graph illustrating the raw activation of an exemplary highly relevant filters according to some examples of the disclosure. For example, FIG. 3A illustrates an exemplary binary segmentation mask 314 during the systole phase of the heartbeat superimposed on exemplary activations $A(t)_k^j$ 312 for the neuron that is the most relevant for calculating systolic blood pressure. FIG. 3A also illustrates an exemplary heatmap 310 representing the activity level of the most relevant neuron overlaid on the SCG provided to the model. In heatmap 310, lighter points represent relatively high neuron activity levels, darker points represent relatively low neuron activity levels, and blank sections indicate lowest neuron activity levels (e.g., during diastole).

Likewise, FIG. 3B illustrates an exemplary binary segmentation mask 322 during the diastole phase of the heartbeat superimposed on exemplary activations $A(t)_k^j$ 324 for the neuron that is the most relevant for calculating diastolic blood pressure. FIG. 3B also illustrates an exemplary heatmap 320 representing the activity level of the most relevant neuron overlaid on the SCG provided to the model. In heatmap 320, lighter points represent relatively high neuron activity levels, darker points represent relatively low neuron activity levels, and blank sections indicate lowest neuron activity levels (e.g., during systole).

In some examples, these neurons activate in response to different phases of the cardiac cycle with almost no overlap. For example, as shown in FIG. 3A, the selected neuron is highly active during systole (e.g., mask 314 high) and less active during diastole (e.g., mask 314 low). Likewise, as another example, as shown in FIG. 3B, the selected neuron is highly active during diastole (mask 324 high) and less active during systole (e.g., mask 324 low). FIG. 3A and FIG. 3B illustrate activity levels of different neurons (e.g., one that is highly relevant during systole and one that highly relevant during diastole). This specialization of neurons can occur without training the network to look for these features. In some examples, neurons with high relevance most strongly contribute to the multi-task learning and disentangling information for estimating systolic and diastolic BP.

In some examples, not all neurons from a baseline model may be important or necessary for a given task. For example, end-to-end networks can learn various implicit patterns about an input signal, even if not trained explicitly for that task. Thus, some of the lowest relevance neurons may cause negative transfer during inference. To overcome this problem, each neuron's Separability, Sj can be calculated to identify the rank order of the neurons based on their relative sensitivity to a particular concept for a dataset. Each neuron's Separability can be computed using Equation 2 as the absolute difference between RS (relevance to systole) and RD (relevance to diastole) over all input samples.

$$S^j = \frac{\left|\sum_i R_S^{i,j} - \sum_i R_D^{i,j}\right|}{\sum_i} \quad (2)$$

Figure 3C:
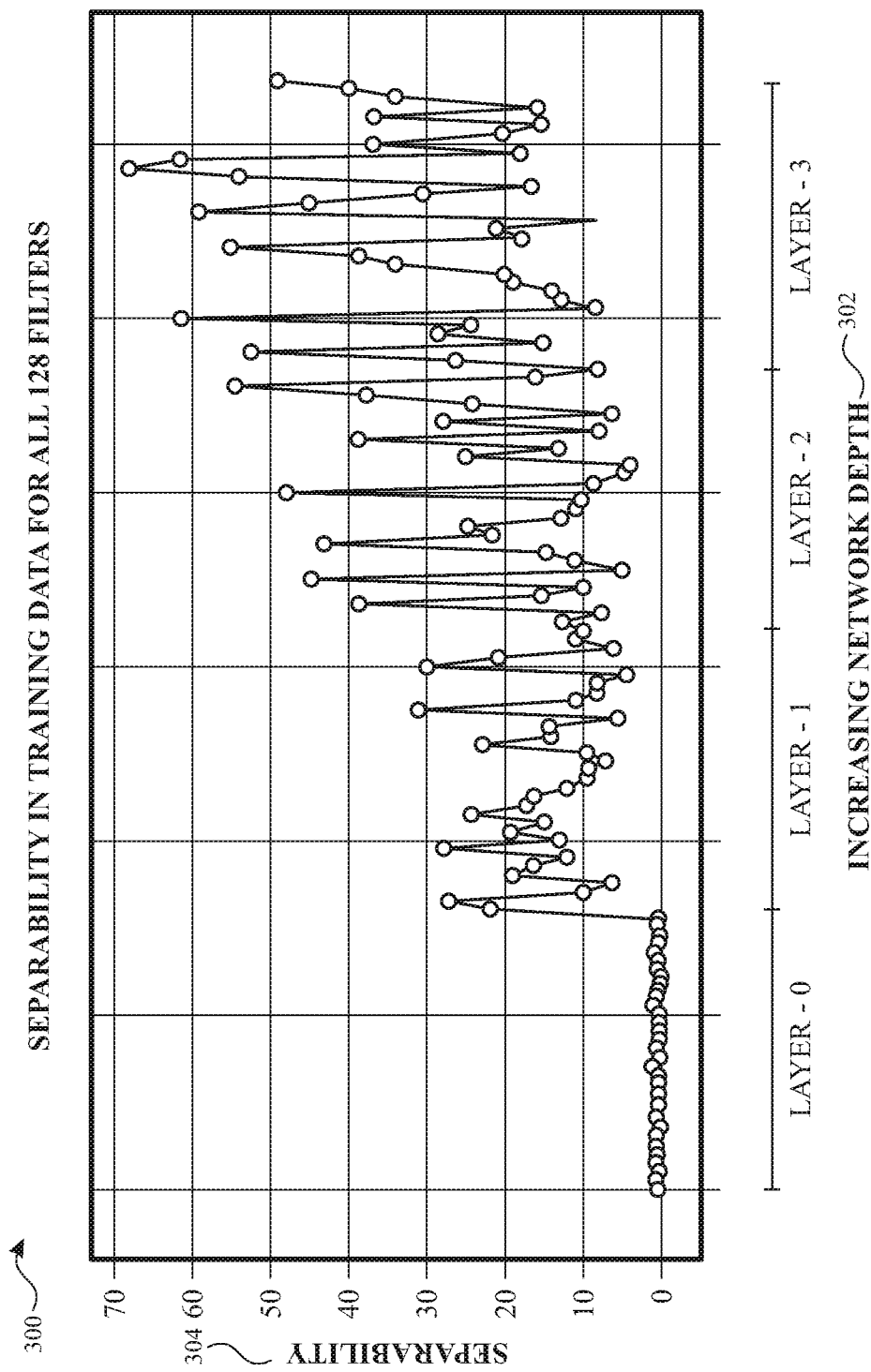

FIG. 3C illustrates the separability of neurons in an exemplary artificial neural network according to some examples of the disclosure. The graph 300 illustrates the separability 304 of each neuron in the network. The x-axis 302 of the graph 300 represents each neuron in the network arranged by layer. For example, layer-0 can receive the inputs (e.g., an SCG) to the neural network and layer-3 can output the final output (e.g., systolic and diastolic blood pressures) of the neural network.

The graph 300 can show, via the separability metric, the network's ability to encode the information about the two known concepts with increasing depth. The first layer (e.g., layer-0) can behave like a low-pass filter with almost no sensitivity to the segmented morphology ($S^{0-31}$~0). The next two layers (e.g., layer-1 and layer-2) can show increased sensitivity to the concepts, with the last layer (e.g., layer-3) showing best encoding concepts in individual neurons resulting in the highest values for separability.

In some examples, modeling human data can be challenging because the models may not generalize well on data from unseen subjects. This challenge in generalization can be due to the information change that is attributed to inter-subject variability. Thus, in some examples, it can be advantageous to prune the model using a small amount of unseen user's data to find an optimal, personalized architecture based on the baseline model by leveraging the concepts of relevance and separability.

In some examples, an unseen user can provide blood pressure cuff readings and IMU readings during a sample period of about thirty seconds. This data can be used to prune the baseline model for future use to calculate that person's blood pressure from IMU data.

First, the feed-forward operation can be run for k iterations with only the top-k (k=1, 2, . . . 32) neurons activated in the final layer (e.g., layer-3), where a neuron can be added for each iteration. For example, the first iteration is ran with only the most separable neuron activated in the final layer and the second iteration is ran with both the most separable neuron and the next most separable neuron activated, and so on. All neurons can remain on in the other layers (e.g., layer-0, layer-1, and layer-2). In some examples, the subsequent connections can also be adjusted to account for the neurons that are off.

These 32 predictions of SBP and DBP can then be compared with the reference measurement (e.g., blood pressure cuff data) from the session used for pruning. In some examples, the mean absolute error (MAE) can be plotted as a function of how many neurons (e.g., filters) are active in the final layer of the network, as described in more detail below with reference to FIGS. 4A-4C.

Figure 4A:
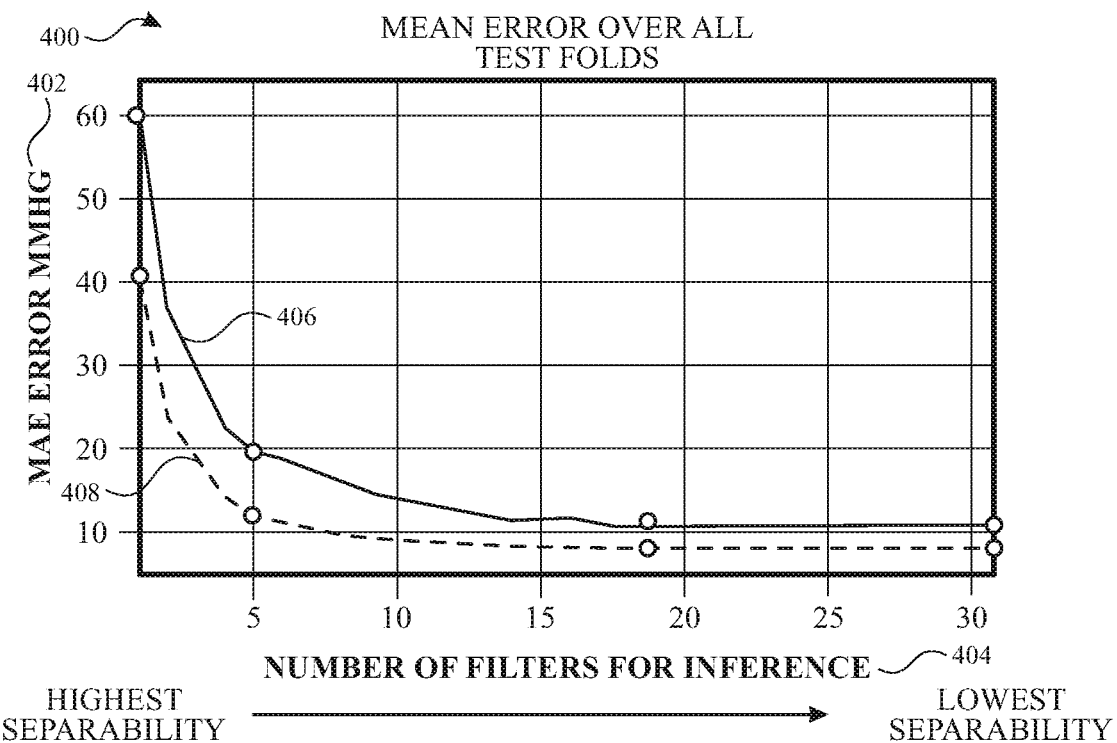
FIGS. 4A-4C illustrate exemplary relationships between testing errors and the number of filters in an artificial neural network according to some examples of the disclosure.
Figure 4B:
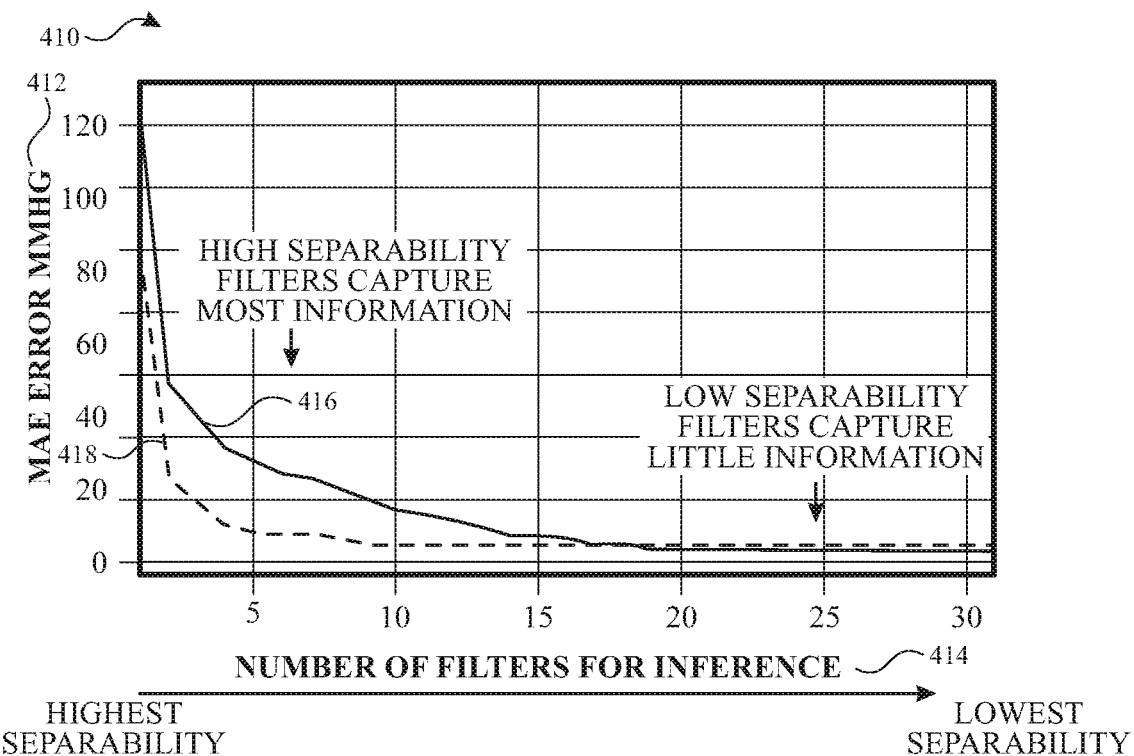
Figure 4C:
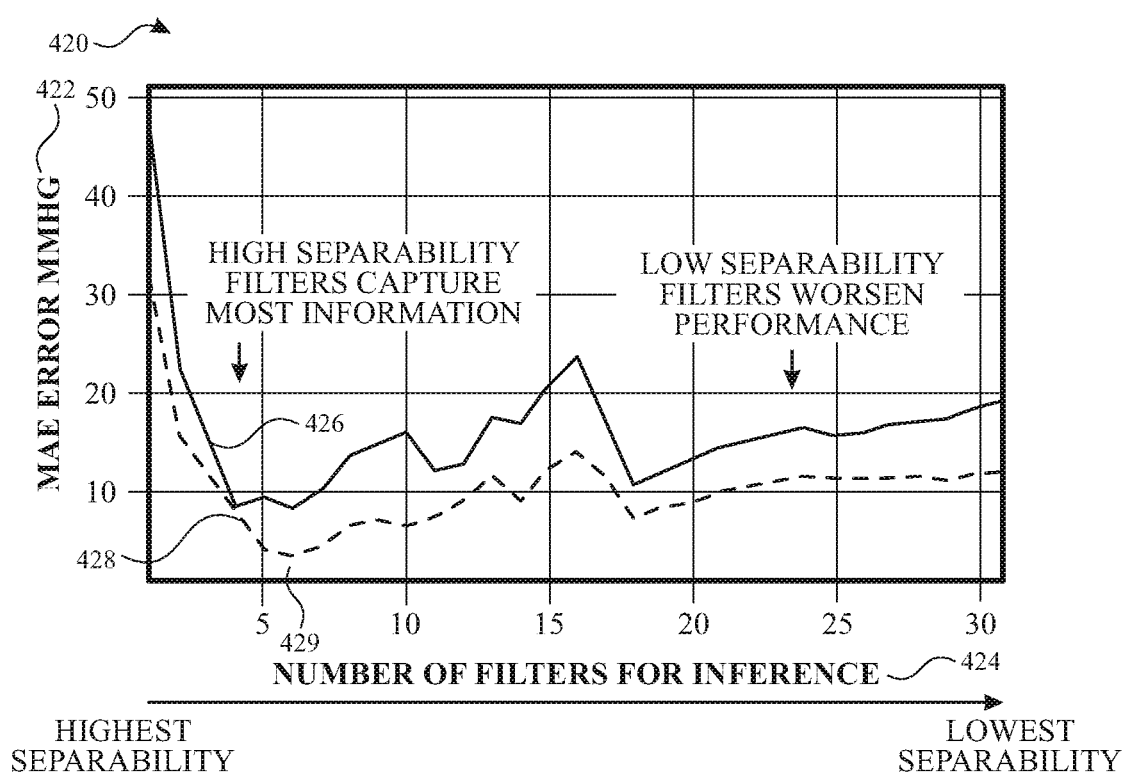

FIGS. 4A-4C illustrate exemplary relationships between testing errors and the number of filters in an artificial neural network according to some examples of the disclosure. FIG. 4A shows an example of the change in error 402 for systolic blood pressure 406 and diastolic blood pressure 408 as more filters 404 are added (top-k) based on separability. For example, the graph 400 in FIG. 4A shows the mean absolute error in mmHg across all subjects. A sharp decrease in error after the first few configurations (e.g., around 5 filters used) can be attributed to the critical role of high separability filters.

In some examples, the mean absolute error can have a similar or different shaped curve to graph 400 for an individual subject. Thus, in some examples, the model can adapted for each unseen user by plotting the mean average error versus the number of highest-level filters used for the individual. As described above, the plot can be constructed using a small amount of SCG data and blood pressure cuff data collected for the purpose of adapting the neural network for that particular individual. The pruned model can then be used for inference for the remaining sessions, avoiding the need for retraining or more data from the target domain. In some examples, about 30 seconds of data from the end of the first session was used to prune and adapt the model.

FIG. 4B illustrates the relationship between testing errors and the number of filters in an artificial neural network for a low-error subject according to some examples of the disclosure. FIG. 4B illustrates a graph 410 of the MAE 412 for systolic blood pressure 416 and diastolic blood pressure 418 versus the number 414 of top-level filters used. The graph 410 has a similar shape to the graph 400 of MAE for all subjects described above with reference to FIG. 4A. Thus, for low-error subjects, the model can be pruned according to an asymptote of the error curves 416 and 418, such as pruning in the range of 5-20 top-level filters, depending on the level of accuracy and computational complexity desired.

FIG. 4C illustrates the relationship between testing errors and the number of filters in an artificial neural network for a high-error subject according to some examples of the disclosure. FIG. 4C illustrates a graph 420 of the MAE 422 for systolic blood pressure 426 and diastolic blood pressure 428 versus the number 424 of top-level filters used. Although graph 420 demonstrates a decrease in MAE 422 between 1 filter used and 5 filters used that is similar to the decrease in this filter range for graphs 400 and 410, after 6 filters, the MAE 422 begins to increase again as more lower-separability filters are added to the top layer of the network. Thus, for high-error subjects, it can be advantageous to select the number of top-level filters that has the lowest errors by multiplying the systolic blood pressure 426 error and the diastolic blood pressure 428 error for each point and selecting the number of filters for which the product of the errors is a minimum. For example, point 429 on graph 420 can be the point with the minimum error product, which can occur when 6 filters are activated in the top level of the network. Thus, for this subject, subsequent inference using the model can be performed using 6 top-level filters.

Figure 5:
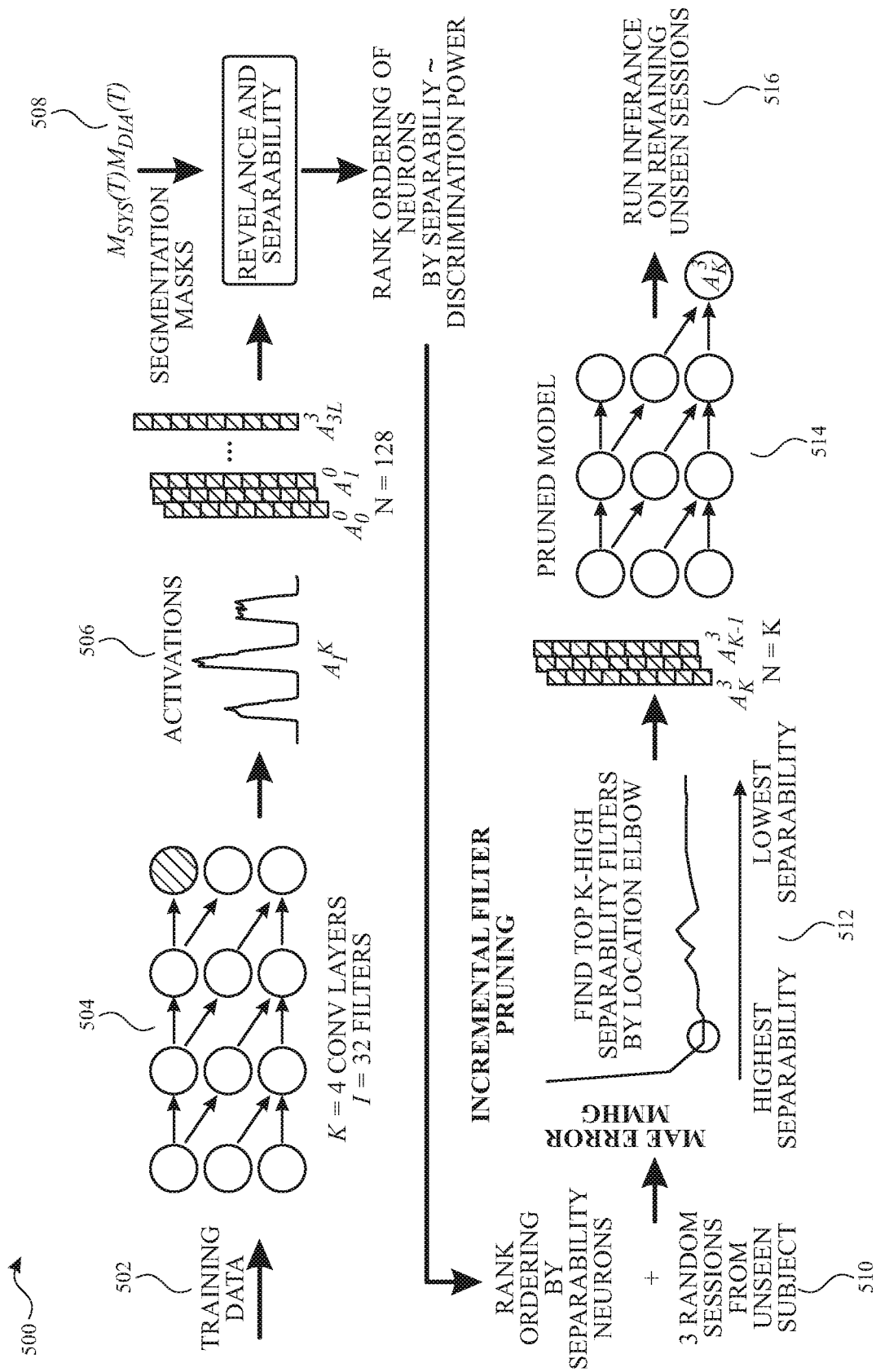
FIG. 5 illustrates an exemplary process for training, pruning, and using an artificial neural network according to some examples of the disclosure.

FIG. 5 illustrates an exemplary process for training, pruning, and using an artificial neural network according to some examples of the disclosure. Process 500 can be performed in accordance with one or more examples described above with reference to FIGS. 1-4C. One or more steps of process 500 (and, likewise, one or more examples described above with reference to FIGS. 1-4C) can be stored on a non-transitory computer-readable storage medium that can be executed by an electronic device with one or more processors. For example, a wearable device 114 or another electronic device in communication with wearable device 114, IMUs 102-112, or another motion data-collecting device can implement one or more of the examples described herein with reference to FIGS. 1-5.

At 502, training data from multiple subjects can be collected. The training data can include motion data collected by one or more IMUs 102-112, a wearable device 114, or another electronic device outfitted with one or more accelerometers and/or gyroscopes. The training data also includes corresponding blood pressure measurements collected using a blood pressure cuff 116 or other suitable instrumentation. For example, data from 13 subjects can be collected or from a different number of subjects.

At 504, the training data can be supplied to the neural network to train the neural network to calculate systolic and diastolic blood pressure from motion data. In some examples, the neural network can have four layers, with 32 filters per layer. In some examples, different network sizes and structures can be used. The trained network can be a baseline model that can be further refined through pruning, for example.

At 506, the activations of the filters of the neural network can be observed. For example, activations of the top-level filters during each of the systolic and diastolic phases of the heartbeat can be observed as described above with reference to FIGS. 3A-3C. In some examples, identifying the activation of each filter can provide information about the relevance and separability of each filter. For example, the activations of all of the top-level filters can be observed. In some examples, the activations of filters in other layers of the network can be observed as well.

At 508, the relevance and separability of each filter can be determined, such as by using equations (1) and (2) discussed above. In some examples, segmentation masks corresponding to the systole and diastole phases of the heartbeat can be applied to the activation data to determine that activation of each filter during each of these phases, as described above with reference to FIGS. 3A-3C. Determining the activation of each filter during each of the systole and diastole phases can be used to calculate the relevance of each filter to each of systolic and diastolic blood pressures, for example, according to equation (1). In some examples, the relevance of each filter to the systolic and diastolic blood pressures can then be used to calculate the separability of the filter according to equation (2). Once the separability of all of the filters (e.g., all top-level filters or all filters in one or more selected layers) has been calculated, the filters can be ranked in order of separability, for example.

At 510, data from an unseen user can be applied to the baseline model multiple times, each time with a different number top-layer filters ranked by separability. The unseen subject can provide motion and blood pressure data collected in a manner similar to, but in some examples less extensive (e.g., for less time or fewer sessions) than, the manner in which training data 502 was collected, for example. In some examples, the motion data is processed by the baseline model n times, each time with 1, 2, . . . , n top-layer most separable filters activated. The mean absolute error of the calculated systolic and diastolic blood pressure compared to the measured systolic and diastolic blood pressure can be calculated for each run.

At 512, the optimal number of top-level high separability filters can be determined. For example, as described above with reference to FIGS. 4A-4C, a minimum error product or an asymptote of the error curve can be identified for the individual subject.

At 514, the individually-pruned network can be generated by pruning according to 512, for example. In some examples, pruning based on data from an individual subject can produce a model that calculates blood pressure with minimum errors for that individual.

At 516, inference can be ran using the individually-pruned network. For example, the individual subject can provide further motion data to the network to calculate blood pressure. In this way, the individual is able to obtain an estimate of their blood pressure without the use of a blood pressure cuff or blood pressure measurement instrument other than one or more IMUS 102-112, a wearable device 116, or other device that collects motion data. As discussed above, aspects in of the present technology include the gathering and use of physiological information. The technology may be implemented along with technologies that involve gathering personal data that relates to the user's health and/or uniquely identifies or can be used to contact or locate a specific person. Such personal data can include demographic data, date of birth, location-based data, telephone numbers, email addresses, home addresses, and data or records relating to a user's health or level of fitness (e.g., vital signs measurements, medication information, exercise information, etc.).

In some examples, an individually-pruned neural network can be used to calculate blood pressure based on a SCG. However, the disclosure is not limited to these applications. One or more examples discussed above related to determining the relevance and separability of one or more filters of a network, ranking the filters by separability, and pruning the network according to an individual to reduce errors can be applied to other applications. For example, one or more examples of the disclosure can be applied personalization of neural networks, such as to adapting neural networks for human-computer interaction applications, overcoming inter-user variability to due natural traits (e.g., accent, voice, speed, prosody etc.) in speech, and personalization of news, music content, etc. using "relevance" metrics. One or more examples of the disclosure can be applied to phenotyping for genomic health, such as discovering specific signal patterns and shapes that are unique to a person or group of people (e.g., phenotypes), analysis of the relevant neurons as identified by the metric (e.g., Relevance can reveal groups of people and the change in their health (with change in habits/phenotypes). This can help with designing new personalized coaching plans based on how each individual changes), and drug discovery targeted to specific traits in the data when discovered using the relevance and separability metrics. Some examples of the disclosure can be applied to biomarker detection, such as discovering new biomarkers used and learned by a neural network to make decisions (e.g., sleep metrics based on respiration signals) and other conditions that can be detected using signals from wearable devices, such as voice and motion sensors. Some examples of the disclosure can be applied to model compression, such as leveraging the smaller footprint of a pruned neural network which can save computation complexity, memory, and power on electronic devices, such as mobile devices and enabling each user to have a different configuration of a baseline neural network.

The present disclosure recognizes that a user's personal data, including physiological information, such as data generated and used by the present technology, can be used to the benefit of users. For example, an SCG can allow a user to gain insight into their blood pressure, which can provide the user with information about their heart and overall health.

The present disclosure contemplates that the entities responsible for the collection, analysis, disclosure, transfer, storage, or other use of such personal data will comply with well-established privacy policies and/or privacy practices. In particular, such entities should implement and consistently use privacy policies and practices that are generally recognized as meeting or exceeding industry or governmental requirements for maintaining personal information data private and secure. Such policies should be easily accessible by users, and should be updated as the collection and/or use of data changes. Personal information from users should be collected for legitimate and reasonable uses of the entity and not shared or sold outside of those legitimate uses. Further, such collection/sharing should require receipt of the informed consent of the users. Additionally, such entities should consider taking any needed steps for safeguarding and securing access to such personal information data and ensuring that others with access to the personal information data adhere to their privacy policies and procedures. Further, such entities can subject themselves to evaluation by third parties to certify their adherence to widely accepted privacy policies and practices. The policies and practices may be adapted depending on the geographic region and/or the particular type and nature of personal data being collected and used.

Despite the foregoing, the present disclosure also contemplates embodiments in which users selectively block the collection of, use of, or access to, personal data, including physiological information. For example, a user may be able to disable hardware and/or software elements that collect physiological information. Further, the present disclosure contemplates that hardware and/or software elements can be provided to prevent or block access to personal data that has already been collected. Specifically, users can select to remove, disable, or restrict access to certain health-related applications collecting users' personal health or fitness data.

Therefore, according to the above, some examples of the disclosure are directed to a method, comprising determining activity levels of one or more filters of a first neural network while the first neural network processes first data; calculating a relevance of each of one or more of filters of a first neural network based on activity levels of the one or more filters; calculating a separability of each of the one or more filters based on relevance of each of the one or more filters;

constructing a second neural network by modifying the first neural network to deactivate a first number of the one or more filters based on the separability of the one or more filters; analyzing second data with the second neural network; calculating a first mean absolute error of the analysis of the second data with the second neural network; constructing a third neural network by modifying the first neural network to deactivate a second number of the one or more filters based on the separability of the one or more filters; analyzing the second data with the third neural network; calculating a second mean absolute error of the analysis of the second data with the third neural network; and comparing the first mean absolute error to the second mean absolute error. Additionally or alternatively, in some examples, the method further includes segmenting the first data into first phases and second phases; determining the activity levels of the one or more filters during the first phase to determine first activity levels of the one or more filters; determining the activity levels of the one or more filters during the second phase to determine second activity levels of the one or more filters; calculating a first relevance of the one or more filters based on the first activity levels of the one or more filters; and calculating a second relevance of the one or more filters based on the second activity levels of the one or more filters. Additionally or alternatively, in some examples, calculating the separability of the one or more filters includes calculating the difference between the first relevance of the one or more filters and the second relevance of the one or more filters. Additionally or alternatively, in some examples, the method further includes ranking the one or more filters in order of separability from most-separable to least-separable, wherein: deactivating the first number of the one or more filters includes deactivating the first number of least-separable filters of the one or more filters, and deactivating the second number of the one or more filters includes deactivating the second number of least-separable filters of the one or more filters. Additionally or alternatively, in some examples, the method further includes constructing a fourth neural network by determining the number of least-separable filters to deactivate that produces a minimum mean absolute error compared to all possible numbers of filters to deactivate. Additionally or alternatively, in some examples, the first data comprises a seismocardiogram (SCG) and the first neural network is configured to determine systolic and diastolic blood pressure based on the SCG.

Some examples of the disclosure are directed to a non-transitory computer-readable storage medium storing instructions that, when executed by an electronic device including one or more processors, causes the electronic device to perform a method comprising: observing activity levels of one or more filters of a first neural network while the first neural network processes first data; calculating a relevance of each of the one or more of filters based on the activity levels of the one or more filters; calculating a separability of each of the one or more filters based on relevance of each of the one or more filters; constructing a second neural network by modifying the first neural network to deactivate a first number of the one or more filters based on the separability of the one or more filters; analyzing second data with the second neural network; calculating a first mean absolute error of the analysis of the second data with the second neural network; constructing a third neural network by modifying the first neural network to deactivate a second number of the one or more filters based on the separability of the one or more filters; analyzing the second data with the third neural network; calculating a second mean absolute error of the analysis of the second data with the third neural network; and comparing the first mean absolute error to the second mean absolute error.

Some examples of the disclosure are directed to a method comprising ranking one or more filters of a baseline neural network in order of separability; providing first data and second data to the baseline neural network that is configured to calculate a first property based on the first data, the first property being an estimate of the second data; constructing a first neural network by deactivating a first number of the one or more filters based on the separability of the one or more filters; analyzing the first data with the first neural network; calculating a first mean absolute error of the analysis of the first data with the first neural network compared to the second data; constructing a second neural network by deactivating a second number of the one or more filters based on the separability of the one or more filters; analyzing the first data with the second neural network; calculating a second mean absolute error of the analysis of the first data with the second neural network compared to the second data; in accordance with a determination that the first mean absolute error is less than the second mean absolute error, using the first neural network to perform analysis on subsequent data; and in accordance with a determination that the second mean absolute error is less than the first mean absolute error, using the second neural network to perform analysis on the subsequent data.

Some examples of the disclosure are directed to a non-transitory computer-readable storage medium storing instructions that, when executed by an electronic device including one or more processors, causes the electronic device to perform a method comprising ranking one or more filters of a baseline neural network in order of separability; providing first data and second data to the baseline neural network that is configured to calculate a first property based on the first data, the first property being an estimate of the second data; constructing a first neural network by deactivating a first number of the one or more filters based on the separability of the one or more filters; analyzing the first data with the first neural network; calculating a first mean absolute error of the analysis of the first data with the first neural network compared to the second data; constructing a second neural network by deactivating a second number of the one or more filters based on the separability of the one or more filters; analyzing the first data with the second neural network; calculating a second mean absolute error of the analysis of the first data with the second neural network compared to the second data; in accordance with a determination that the first mean absolute error is less than the second mean absolute error, using the first neural network to perform analysis on subsequent data; and in accordance with a determination that the second mean absolute error is less than the first mean absolute error, using the second neural network to perform analysis on the subsequent data.

Some examples of the disclosure are directed to a method comprising constructing a first neural network that accepts a seismocardiogram (SCG) as input and calculates systolic and diastolic blood pressure as outputs; constructing a second neural network by deactivating a plurality of filters of the first neural network based on a first SCG, a first systolic blood pressure, and a first diastolic blood pressure of an individual subject; and calculating, using the second neural network, a second systolic blood pressure and second diastolic blood pressure of the individual subject using a second SCG of the individual subject.

Some examples of the disclosure are directed to a non-transitory computer-readable storage medium storing instructions that, when executed by an electronic device including one or more processors, causes the electronic device to perform a method, comprising: constructing a first neural network that accepts a seismocardiogram (SCG) as input and calculates systolic and diastolic blood pressure as outputs; constructing a second neural network by deactivating a plurality of filters of the first neural network based on a first SCG, a first systolic blood pressure, and a first diastolic blood pressure of an individual subject; and calculating, using the second neural network, a second systolic blood pressure and second diastolic blood pressure of the individual subject using a second SCG of the individual subject.

Although the disclosed examples have been fully described with reference to the accompanying drawings, it is to be noted that various changes and modifications will become apparent to those skilled in the art. Such changes and modifications are to be understood as being included within the scope of the disclosed examples as defined by the appended claims.

The invention claimed is:

1. A method, comprising:
   observing activity levels of one or more filters of a first neural network while the first neural network processes first data from a plurality of subjects;
   calculating a relevance of each of one or more of filters of a first neural network based on the activity levels of the one or more filters while the first neural network processes the first data from the plurality of subjects;
   calculating a separability of each of the one or more filters based on relevance of each of the one or more filters;
   constructing a second neural network by modifying the first neural network to deactivate a first number of the one or more filters based on the separability of the one or more filters;
   analyzing second data from an individual subject not included in the plurality of subjects with the second neural network;
   calculating a first mean absolute error of the analysis of the second data from the individual subject with the second neural network;
   constructing a third neural network by modifying the first neural network to deactivate a second number of the one or more filters based on the separability of the one or more filters;
   analyzing the second data from the individual subject with the third neural network;
   calculating a second mean absolute error of the analysis of the second data from the individual subject with the third neural network; and
   comparing the first mean absolute error to the second mean absolute error.

2. The method of claim 1, further comprising:
   segmenting the first data into first phases and second phases;
   determining the activity levels of the one or more filters during the first phase to determine first activity levels of the one or more filters;
   determining the activity levels of the one or more filters during the second phase to determine second activity levels of the one or more filters;
   calculating a first relevance of the one or more filters based on the first activity levels of the one or more filters; and
   calculating a second relevance of the one or more filters based on the second activity levels of the one or more filters.

3. The method of claim 2, wherein calculating the separability of the one or more filters includes calculating a difference between the first relevance of the one or more filters and the second relevance of the one or more filters.

4. The method of claim 1, further comprising:
   ranking the one or more filters in order of separability from most-separable to least-separable, wherein:
      deactivating the first number of the one or more filters includes deactivating the first number of least-separable filters of the one or more filters, and
      deactivating the second number of the one or more filters includes deactivating the second number of least-separable filters of the one or more filters.

5. The method of claim 4, further comprising:
   constructing a fourth neural network by determining the number of least-separable filters to deactivate that produces a minimum mean absolute error compared to all possible numbers of filters to deactivate.

6. The method of claim 1, wherein the first data comprises a seismocardiogram (SCG) and the first neural network is configured to determine systolic and diastolic blood pressure based on the SCG.

7. A non-transitory computer-readable storage medium storing instructions that, when executed by an electronic device including one or more processors, causes the electronic device to perform a method comprising:
   observing activity levels of one or more filters of a first neural network while the first neural network processes first data from a plurality of subjects;
   calculating a relevance of each of the one or more of filters based on the activity levels of the one or more filters while the first neural network processes the first data from the plurality of subjects;
   calculating a separability of each of the one or more filters based on relevance of each of the one or more filters;
   constructing a second neural network by modifying the first neural network to deactivate a first number of the one or more filters based on the separability of the one or more filters;
   analyzing second data from an individual subject not included in the plurality of subjects with the second neural network;
   calculating a first mean absolute error of the analysis of the second data from the individual subject with the second neural network;
   constructing a third neural network by modifying the first neural network to deactivate a second number of the one or more filters based on the separability of the one or more filters;
   analyzing the second data from the individual subject with the third neural network;
   calculating a second mean absolute error of the analysis of the second data from the individual subject with the third neural network; and
   comparing the first mean absolute error to the second mean absolute error.

8. A method comprising:
   ranking one or more filters of a baseline neural network in order of separability while processing data from a plurality of subjects;
   providing first and second data from an individual subject not included in the plurality of subjects to the baseline neural network that is configured to calculate a first property based on the first data, the first property being an estimate of the second data;
   constructing a first neural network by deactivating a first number of the one or more filters based on the separability of the one or more filters while processing the data from the plurality of subjects;

analyzing the first data from the individual subject with the first neural network;

calculating a first mean absolute error of the analysis of the first data from the individual subject with the first neural network compared to the second data from the individual subject;

constructing a second neural network by deactivating a second number of the one or more filters based on the separability of the one or more filters while processing the data from the plurality of subjects;

analyzing the first data from the individual subject with the second neural network;

calculating a second mean absolute error of the analysis of the first data from the individual subject with the second neural network compared to the second data from the individual subject;

in accordance with a determination that the first mean absolute error is less than the second mean absolute error, using the first neural network to perform analysis on subsequent data from the individual subject; and in accordance with a determination that the second mean absolute error is less than the first mean absolute error, using the second neural network to perform analysis on the subsequent data from the individual subject.

9. A non-transitory computer-readable storage medium storing instructions that, when executed by an electronic device including one or more processors, causes the electronic device to perform a method comprising:

ranking one or more filters of a baseline neural network in order of separability while processing data from a plurality of subjects;

providing first and second data from an individual subject not included in the plurality of subjects to the baseline neural network that is configured to calculate a first property based on the first data, the first property being an estimate of the second data;

constructing a first neural network by deactivating a first number of the one or more filters based on the separability of the one or more filters while processing the data from the plurality of subjects;

analyzing the first data from the individual subject with the first neural network;

calculating a first mean absolute error of the analysis of the first data from the individual subject with the first neural network compared to the second data from the individual subject;

constructing a second neural network by deactivating a second number of the one or more filters based on the separability of the one or more filters while processing the data from the plurality of subjects;

analyzing the first data from the individual subject with the second neural network;

calculating a second mean absolute error of the analysis of the first data from the individual subject with the second neural network compared to the second data from the individual subject;

in accordance with a determination that the first mean absolute error is less than the second mean absolute error, using the first neural network to perform analysis on subsequent data from the individual subject; and in accordance with a determination that the second mean absolute error is less than the first mean absolute error, using the second neural network to perform analysis on the subsequent data from the individual subject.

10. A method, comprising:

constructing a first neural network that accepts a seismocardiogram (SCG) as input and calculates systolic and diastolic blood pressure as outputs based on training data from a plurality of subjects;

constructing a second neural network by deactivating a plurality of filters of the first neural network based on a first SCG, a first systolic blood pressure, and a first diastolic blood pressure of an individual subject not included in the plurality of subjects, wherein the plurality of filters that are deactivated are selected based on separability of the filters for determining the systolic blood pressure or the diastolic blood pressure based on the training data from the plurality of subjects; and calculating, using the second neural network, a second systolic blood pressure and second diastolic blood pressure of the individual subject using a second SCG of the individual subject.

11. A non-transitory computer-readable storage medium storing instructions that, when executed by an electronic device including one or more processors, causes the electronic device to perform a method, comprising:

constructing a first neural network that accepts a seismocardiogram (SCG) as input and calculates systolic and diastolic blood pressure as outputs based on training data from a plurality of subjects;

constructing a second neural network by deactivating a plurality of filters of the first neural network based on a first SCG, a first systolic blood pressure, and a first diastolic blood pressure of an individual subject not included in the plurality of subjects, wherein the plurality of filters that are deactivated are selected based on separability of the filters for determining the systolic blood pressure or the diastolic blood pressure based on the training data from the plurality of subjects; and calculating, using the second neural network, a second systolic blood pressure and second diastolic blood pressure of the individual subject using a second SCG of the individual subject.

12. The method of claim 1, wherein the relevance of each of the one or more filters that the separability of each of the one or more filters is based on is a relevance of each of the one or more filters to determining one of a plurality of outputs of the first neural network.

13. The method of claim 8, wherein the separability of the one or more filters is based on is a relevance of each of the one or more filters to determining one of a plurality of outputs of the first neural network.

14. The non-transitory computer-readable storage medium of claim 7, wherein the method further comprises:

segmenting the first data into first phases and second phases;

determining the activity levels of the one or more filters during the first phase to determine first activity levels of the one or more filters;

determining the activity levels of the one or more filters during the second phase to determine second activity levels of the one or more filters;

calculating a first relevance of the one or more filters based on the first activity levels of the one or more filters; and calculating a second relevance of the one or more filters based on the second activity levels of the one or more filters.

15. The non-transitory computer-readable storage medium of claim 14, wherein calculating the separability of the one or more filters includes calculating a difference between the first relevance of the one or more filters and the second relevance of the one or more filters.

16. The non-transitory computer-readable storage medium of claim 7, wherein the method further comprises:
ranking the one or more filters in order of separability from most-separable to least-separable, wherein:
deactivating the first number of the one or more filters includes deactivating the first number of least-separable filters of the one or more filters, and deactivating the second number of the one or more filters includes deactivating the second number of least-separable filters of the one or more filters.

17. The non-transitory computer-readable storage medium of claim 16, wherein the method further comprises:
constructing a fourth neural network by determining the number of least-separable filters to deactivate that produces a minimum mean absolute error compared to all possible numbers of filters to deactivate.

18. The non-transitory computer-readable storage medium of claim 7, wherein the first data comprises a seismocardiogram (SCG) and the first neural network is configured to determine systolic and diastolic blood pressure based on the SCG.

\* \* \* \* \*